(12) United States Patent
Coplen, II

(10) Patent No.: US 7,687,028 B1
(45) Date of Patent: Mar. 30, 2010

(54) SEQUENTIAL, TIME-INTEGRATED COLLECTOR OF PRECIPITATION, GROUND WATER, AND SURFACE WATER FOR ANALYSIS OF ISOTOPES

(75) Inventor: Tyler Benjamin Coplen, II, Reston, VA (US)

(73) Assignee: The United States of America as represented by the Secretary of the Interior, Washington, DC (US)

( * ) Notice: Subject to any disclaimer, the term of this patent is extended or adjusted under 35 U.S.C. 154(b) by 995 days.

(21) Appl. No.: 11/401,010

(22) Filed: Apr. 6, 2006

(51) Int. Cl.
*B01D 61/18* (2006.01)
*G01N 1/34* (2006.01)

(52) U.S. Cl. .............................. 422/67; 422/63; 422/64; 422/99; 73/863.01; 73/863.41; 73/863.42; 73/863.43

(58) Field of Classification Search .................. 422/63, 422/64, 67, 99, 100, 102–104; 73/170.17, 73/170.23, 863.01–863.02, 863.51–863.52, 73/863.56, 864, 864.51, 864.58–864.63, 73/864.91
See application file for complete search history.

(56) References Cited

U.S. PATENT DOCUMENTS

| | | | | |
|---|---|---|---|---|
| 3,213,669 | A | * | 10/1965 | Taft et al. .................... 73/23.35 |
| 3,958,457 | A | * | 5/1976 | Mink ....................... 73/170.21 |
| 4,022,059 | A | | 5/1977 | Schontzler et al. |
| 4,140,011 | A | | 2/1979 | Krupa et al. |
| 4,697,462 | A | | 10/1987 | Daube, Jr. et al. |
| 4,732,037 | A | * | 3/1988 | Daube et al. .............. 73/170.17 |
| 5,091,863 | A | | 2/1992 | Hungerford et al. |
| 5,339,700 | A | | 8/1994 | Wright et al. |
| 5,408,892 | A | | 4/1995 | Kawanami et al. |
| 5,441,071 | A | | 8/1995 | Doherty et al. |
| 5,576,503 | A | | 11/1996 | Nabity et al. |
| 6,152,189 | A | | 11/2000 | Wright et al. |
| 6,742,404 | B2 | | 6/2004 | Smith et al. |

OTHER PUBLICATIONS

Ecotech Model 200 Automatic Rainwater Sampler; Ecotech Pty Ltd., 12 Apollo Court, Blackburn, Victoria, Australia; web site printout, pp. 1-4, http://www.ecotech.com.au/rainwat.htm.
Teledyne ISCO 6712 Full-Size Portable Sampler; Teledyne Isco Inc., 4700 Superior St., Lincoln, NE; web site printout, pp. 1-3, http://www.isco.com/products/products3.asp?PL=201101010.

(Continued)

*Primary Examiner*—Jill Warden
*Assistant Examiner*—Cedric Chan
(74) *Attorney, Agent, or Firm*—Joan Gilsdorf

(57) ABSTRACT

A sequential, time-integrated collector having an electronic controller that actuates either of two electrically-actuated valves, each connected to a water reservoir. At a preset time interval (e.g., every 30 minutes), time-integrated water samples are transferred into sample vials in a multi-sample carousel. Evaporation that could change the isotopic composition of a precipitation sample is minimized by sealing the opening of each sample vial by pressing each vial against a flat, low-friction surface, such as a Teflon® sheet, from the time each sample vial is filled until it is removed from the collector.

13 Claims, 6 Drawing Sheets

OTHER PUBLICATIONS

Teledyne ISCO 6712C Compact Portable Sampler, Teledyne Isco Inc., 4700 Superior St., Lincoln, NE; web site printout, pp. 1-3, http://www.isco.com/products/products3.asp?PL=201101020.

Teledyne ISCO 3700 Full-Size Portable Sampler, Teledyne Isco Inc., 4700 Superior St., Lincoln, NE; web site printout, pp. 1-3, http://www.isco.com/products/products3.asp?PL=201101030.

Teledyne ISCO 3700C Compact Portable Sampler, Teledyne Isco Inc., 4700 Superior St., Lincoln, NE; web site printout, pp. 1-3, http://www.isco.com/products/products3.asp?PL=201101040.

Teledyne ISCO GLS Compact Composite Sampler, Teledyne Isco Inc., 4700 Superior St., Lincoln, NE; web site printout, pp. 1-2; http://www.isco.com/products/products3.as?PL=201102010.

Teledyne ISCO 3710 Composite-only Portable Sampler; Teledyne Isco Inc., 4700 Superior St., Lincoln, NE; web site printout, pp. 1-3, http://www.isco.com/products/products3.asp?PL=201102020.

GENEQ Model TPC-3000 Total Precipitation Collector; GENEQ Inc., 8047 Jarry E., Montreal, Quebec, Canada, H1J 1H6; web site printout, pp. 1-2, http://www.geneq.com/catalog/en/tps_3000.html.

Eigenbrodt NSA 181/KHE Precipitation Collector, G.K.Walter Eigenbrodt, Baurat-Wiese-Strasse 68, D-21255 Königsmoor, Germany; web site printout, pp. 1-3, http://www.eigenbrodt.de/front_content.php?idcat=51&lang=1&client=1.

NILU Precipitation collector; NILU Products AS, Instituttveien 18, P.O. Box 100, NO-2027 Kjeller, Norway; web site printout, pp. 1-2, http://www.nilu.no/products/files/products/pc/particulate_collector.pdf.

Loda Electronics Model 2001 Precipitation Collector Loda Electronics Co., 307 South Elm, P.O.Box 207, Loda IL; web site printout, pp. 1-7, http://www.lodaelectronics.com/nadp.html.

* cited by examiner

SEQUENTIAL, TIME-INTEGRATED COLLECTOR OF PRECIPITATION, GROUND WATER, AND SURFACE WATER FOR ANALYSIS OF ISOTOPES

STATEMENT OF GOVERNMENT INTEREST

The invention described herein may be manufactured and used by or for the Government of the United States of America for government purposes without the payment of any royalties therefore.

BACKGROUND

The present invention is directed, in general, to water sample collectors and, more particularly, to the sequential, time-integrated collection of precipitation, surface water, and ground water samples for analysis.

Large land-falling cyclones produce more than 8 inches of rain in 24 hours and impact the West Coast of the United States, particularly Northern California. In such hydrologic events, the amounts of chemicals and the amounts of isotopes vary in precipitation. The concentrations or relative changes in amounts of chemical constituents or isotopes may provide information to understand physical processes in these complex systems. To determine the relative amounts of oxygen and hydrogen isotopes, precipitation samples need to be collected from these storms at 15- or 30-minute intervals over a period of 24 to 48 hours. Increased understanding of these storms should improve forecasting and allow the National Weather Service of the National Oceanic and Atmospheric Administration (NOAA) to alert earlier the public, the military, and emergency services of these storms.

Various types of liquid sample collectors have been designed. Some collectors contain only one collection vessel, such as a bottle, and are used in bulk precipitation collection for acid-rain studies, for example. While other collectors contain 8 or 24 bottles, these collectors only allow 4 or 12 hours worth of collections, respectively, assuming 30-minute collection intervals. These collectors are inadequate for applications in which 48 hours worth of collections at 30-minute collection intervals are needed. For these types of applications, at least 96 collection vessels are needed to collect at least 96 separate water samples.

Collectors with sample vessels having volumes of 0.5 liter or greater have been used. These sample vessels are unsatisfactory due to the amount of headspace and consequent evaporation that results when low volume (e.g., 0.5 mL to 1 mL) precipitation samples are collected. Evaporation of water from a sample vessel after collection leads to isotopic fractionation, which changes the relative amounts of the hydrogen and oxygen isotopes of the water. To minimize evaporation of low volume samples, collectors are needed that use small bottles (e.g., about 20 mL in volume) to reduce headspace, and also that seal the bottles after collecting each sample.

There are also collectors that collect samples instantaneously or intermittently. These types of collectors typically load a fixed quantity of water at a specific time or at specific times, without collecting and homogenizing the fluid over a time interval before drawing a sample. These types of collectors are inadequate to accurately determine the relative amounts of isotopes in precipitation. To accurately determine the amounts of isotopes, time-integrated samples are needed. In other words, each sample collected needs to be representative of the entire collection interval for that sample. Otherwise, important information can be missed if the fluid is changing, such as the precipitation during a storm. For example, a narrow peak can be missed in a ground water or surface water tracer test when an instantaneous sample is collected at a predetermined interval.

Thus, a precipitation collector is needed that can collect multiple sequential, time-integrated samples as small as 0.5 mL at, for example, 30-minute intervals over an extended period of time, such as 48 hours or longer, and that can also minimize sample evaporation or hold it as close to zero as possible.

SUMMARY

It is an aspect of the present invention to provide a method and apparatus for the unattended collection of sequential, time-integrated water samples at preset time intervals over the course of a hydrologic event or test to determine amounts of isotopes or water quality.

Another aspect of the present invention is to provide a method and apparatus for the unattended collection of sequential, time-integrated water samples for ground water and surface water tracer tests.

Another aspect of the present invention is to provide a method and apparatus for the unattended collection of sequential, time-integrated water samples as small as about 0.5 mL at 15- to 30-minute time intervals over 24- to 48-hour periods or longer.

Another aspect of the present invention is to provide a method and apparatus for the unattended collection of sequential, time-integrated water samples in which multiple sample vials are sealed after each vial receives a sample to prevent evaporation.

These and other aspects are achieved according to the present invention by providing a sequential, time-integrated collector that collects multiple water samples as small as about 0.5 mL in multiple sample vials at preset intervals over an extended period of time. The collector includes an electronic controller that receives a start signal from various inputs, such as a manual push button, a timer, a cell phone, or a rain sensor. Once started, the controller actuates either of two electrically-actuated valves, each connected to a water reservoir. At preset intervals, water samples are transferred into plastic or glass sample vials in a multi-sample carousel. Evaporation that could change the isotopic composition of a precipitation sample is minimized by sealing the opening of each sample vial after it is filled by pressing the mouth of each vial against a flat, low-friction surface, such as a Teflon® sheet. Thus, after loading with a water sample, each vial is exposed to the air for less than 5 minutes, eliminating evaporation. With this approach, 96 or more vials can be used, and samples as small as 0.5 mL can be collected with no change in the relative amounts of hydrogen and oxygen isotopes of the water samples.

According to an embodiment of the present invention, there is provided a water collector for collecting multiple water samples over multiple preset time intervals. The water collector includes a first reservoir that captures water over a preset time interval and homogenizes the water during the preset time interval. A second reservoir receives a predetermined amount of a water sample from the water in the first reservoir at the end of the preset time interval, and any excess water is discharged from the first reservoir. A carousel contains multiple vials, including a first vial and multiple second vials. A sealing plate rests on top of the carousel and has a first opening under which the first vial is positioned. The carousel rotates after the first vial receives the water sample from the second reservoir to move the first vial underneath the sealing plate to seal the first vial, while moving one of the second vials underneath the first opening to receive a next water sample over a next preset time interval. The carousel rotates after each of the second vials has been filled at the end of each successive preset time interval until all of the vials have received a separate water sample. Each vial is sealed after being filled.

According to another embodiment of the present invention, there is provided a method of collecting multiple water samples over multiple preset time intervals, including providing a first reservoir, a second reservoir, a carousel with multiple vials including a first vial and multiple second vials, and a sealing plate resting on a top of the carousel; capturing water in the first reservoir over a preset time interval, the water being homogenized during the preset time interval; transferring a predetermined amount of a water sample from the water in the first reservoir to the second reservoir at the end of the preset time interval, and discharging any excess water from the first reservoir; locating the first vial at a first filling position on the carousel; providing a first opening on the sealing plate corresponding to the first filling position; rotating the carousel after the first vial receives the water sample from the second reservoir to position one of the second vials at the first filling position to receive a next water sample over a next preset time interval, the first vial being rotated away from the first filling position and underneath the sealing plate as the carousel rotates to seal the first vial; and rotating the carousel after each of the second vials has been filled at the end of each successive preset time interval until all of the vials have received a separate water sample, each vial being sealed after being filled.

BRIEF DESCRIPTION OF THE DRAWINGS

The above and other aspects and advantages of the present invention will become apparent and more readily appreciated from the following description, appended claims, and accompanying drawings, of which:

DESCRIPTION

The present invention provides a collector with an electronic controller that receives a start signal from, for example, a manual push button or switch, a timer, a cell phone, or a rain sensor that initiates operation of the collector when it gets wet. Once started, the controller actuates either of two electrically-actuated valves, each connected to a water reservoir. At preset intervals, determined by, for example, a synchronous motor with adjustable gears in the controller or an electronic timing circuit, water samples are transferred into plastic or glass sample vials in a multi-sample carousel. Evaporation that could change the isotopic composition of a precipitation sample is minimized by sealing the opening of each sample vial by pressing each vial against a flat, low-friction surface, such as a Teflon® sheet, from the time each sample vial is filled until it is removed from the collector.

Figure 1:
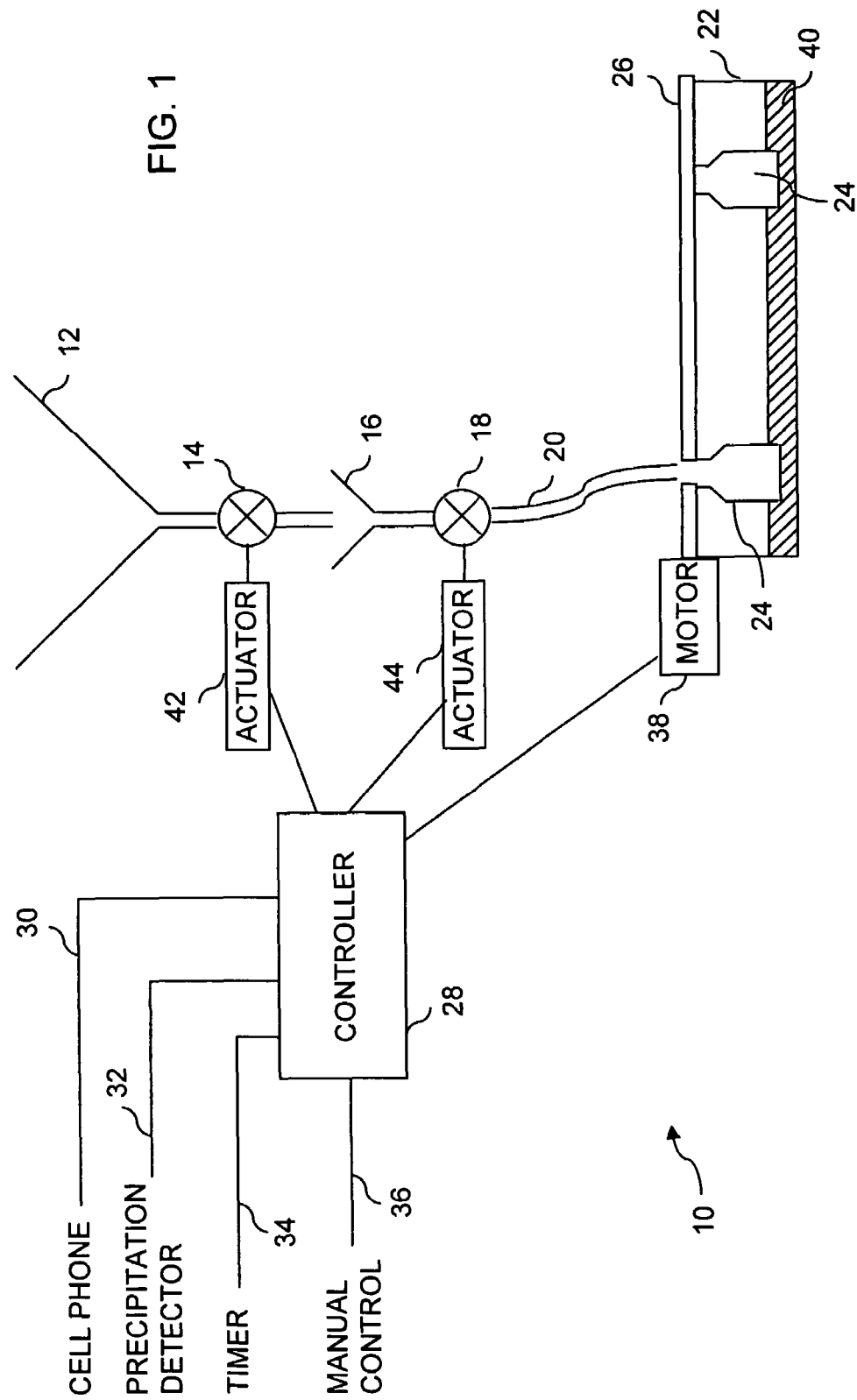
FIG. 1 illustrates a sequential, time-integrated fluid collector according to an embodiment of the present invention.

The operation of a collector 10 according to the present invention can be understood by referring to FIG. 1. Generally, FIG. 1 shows a first reservoir that captures and homogenizes each water sample collected over a preset time interval. The reservoir includes a first funnel 12 and a first valve 14.

A second reservoir extracts a preset maximum amount of water from the total amount of water in the first funnel 12. The second reservoir includes a second funnel 16 and a second valve 18.

A transfer line 20 feeds the water sample by gravity flow from the second funnel 16 to a multi-sample carousel 22. The transfer line 20 may be constructed of flexible plastic, for example.

The carousel 22 holds multiple samples in multiple sample vials 24. After each sample is collected, it is sealed by a sealing plate 26 having a low-friction lower surface to prevent evaporation of the sample and eliminate the accompanying fractionation of oxygen and hydrogen isotopes in water that would otherwise occur.

An electronic controller 28, whose operation can be initiated from a variety of inputs, controls operation of the first valve 14, the second valve 18, and the carousel 22.

The operation of the collector 10 is now described in greater detail.

A start collection program of the controller 28 is initiated from a variety of inputs, such as a cell phone 30, a precipitation detector 32, a timer 34, or a manual push button or switch 36 on the controller 28. Once the controller 28 has started, precipitation samples are loaded into the sample vials 24 at equal time intervals. The sample vials 24 may be constructed of glass or plastic, for example. Only two such vials 24 are shown in FIG. 1 for ease of illustration. The time intervals may be preset by changing gears on a synchronous motor (not shown) that drives cam switches (not shown) in the controller 28. Alternatively, the collector 10 can be controlled using integrated circuit timing.

During a preset time interval (commonly 30 minutes), water is collected and homogenized in the first funnel 12. The first funnel 12 may be constructed of materials such as plastic or aluminum, which can be anodized. If the first funnel 12 is constructed of aluminum, it can be fitted with a thermostat and heater (not shown) to melt snow or hail. The first funnel 12 may have a diameter of about 20 cm, with a maximum sample volume of about 1000 mL, for example. The size of the first funnel 12 is selected to have a volume sufficient to prevent overflow during collection of a water sample during the preset time interval so that none of the sample, which is composited over the preset interval, is lost.

The first funnel 12 is connected to the first valve 14, which is normally closed. After the preset interval, the controller 28 operates a first actuator 42 to open the first valve 14 for sufficient time (about 1 minute) to allow the water to flow directly into the second funnel 16, which holds the water sample that will be transferred to one of the sample vials 24. The amount of time the first valve 14 is open is adjustable. The volume of the second funnel 16 is typically selected to be about 75% of the volume of the sample vials 24 that hold each sample. A size of about 15 mL works well for the second funnel 16. If the amount of water in the first funnel 12 is less than the amount that the second funnel 16 can hold, all of the sample water is captured and transferred to one of the sample vials 24. If the amount of water in the first funnel 12 is greater than the maximum amount of water the second funnel 16 can hold, the excess water spills over the sides of the second funnel 16 and is discarded. For example, if the second funnel 16 holds a maximum of 15 mL of water and the amount of water in the first funnel 12 is greater than 15 mL, all but 15 mL of the composited water spills over the sides of the second funnel 16 and is discarded.

The amount of sample water collected to be transferred into one of the vials 24 may be adjusted by selecting a desired funnel volume for the second funnel 16. Thus, the collector 10 is a variable-amount collector. The volume of each of the sample vials 24 must be greater than that of the water sample from the second funnel 16. Otherwise, water will overflow the sample vials 24 being filled and run down into the bottom of a container 56 (see FIG. 2) that houses components of the carousel 22 and the controller 28. The controller 28 can also be housed in a separate, watertight container (not shown) to allow changes to the controller 28 as samples are being collected.

The controller 28 closes the first valve 14 (FIG. 1). The second funnel 16 is connected to the second valve 18, which is normally closed. The controller 28 operates a second actuator 44 to open the second valve 18 to transfer the sample water in the second funnel 16 through the transfer line 20 (and an opening in the top of the container 56) into one of the sample vials 24 in the carousel 22. The carousel 22 and the transfer line 20 can be heated to just above freezing to prevent ice from forming in the transfer line 20. The excess heat can be used to keep any water in the second funnel 16, the first valve 14, and the second valve 18 from freezing.

After the water sample has been transferred to one of the sample vials 24 (typically, the transfer takes about 10 to about 30 seconds), the controller 28 closes the second valve 18.

The controller 28 activates an electric carousel drive motor 38 to rotate the multi-sample carousel 22 to the next vial 24, which is empty, and the vial 24 just filled is sealed to prevent evaporation. The maximum amount of time any one of the vials 24 may be open is about 5 minutes.

The above operations are repeated until all the vials 24 have been filled.

Sensing that the last vial 24 has been filled (using, for example, a magnetic reed switch, an infrared (IR) optical interrupter detector, or a snap action switch located in the container 56 with the carousel 22), the controller 28 turns off the collector 10. At this point, the filled sample vials 24 have all been sealed to prevent evaporation until being removed from the collector 10.

Figure 2:
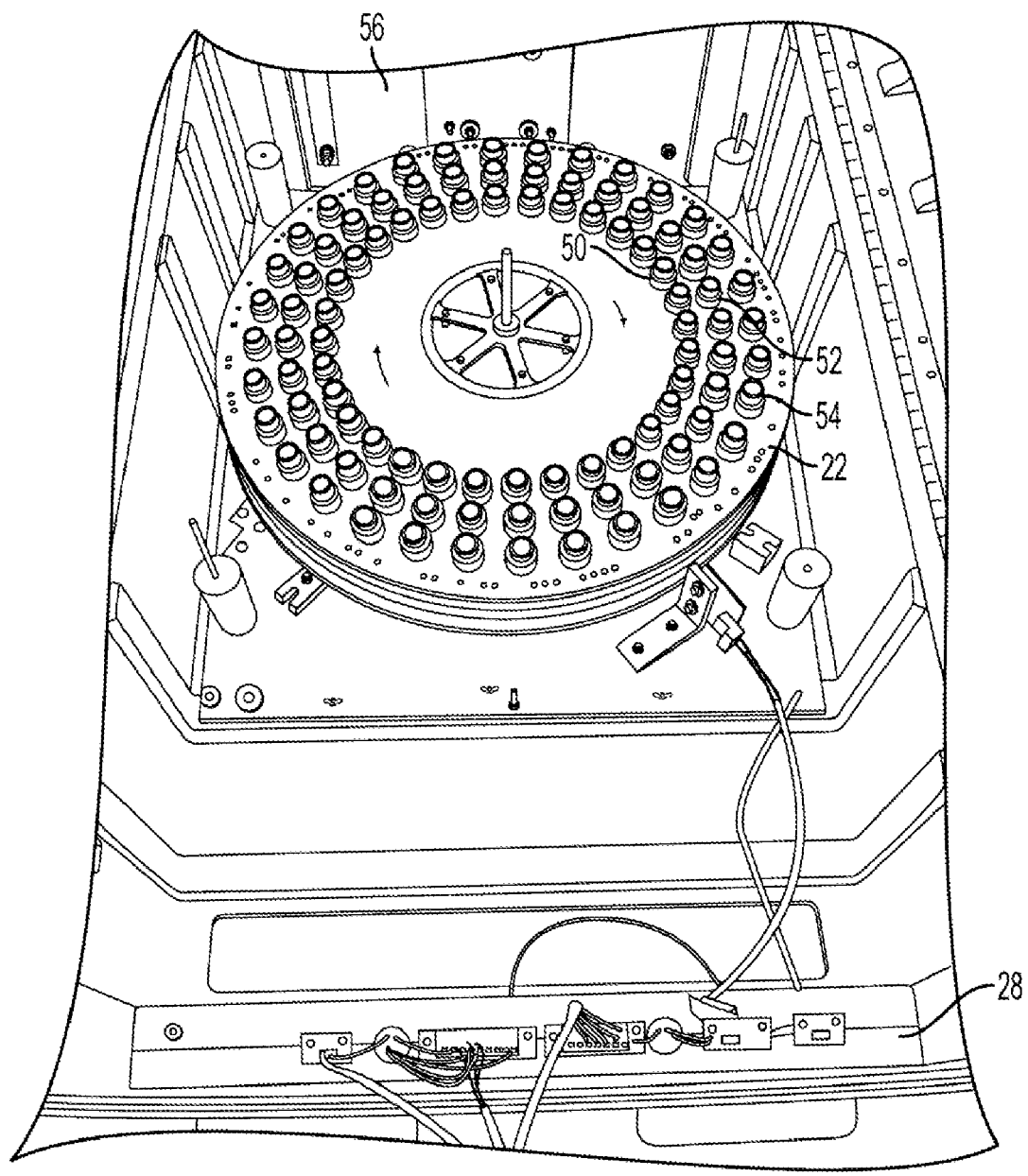
FIG. 2 illustrates the layout of sample vials on a multi-sample carousel for the collector of FIG. 1.
Figure 3:
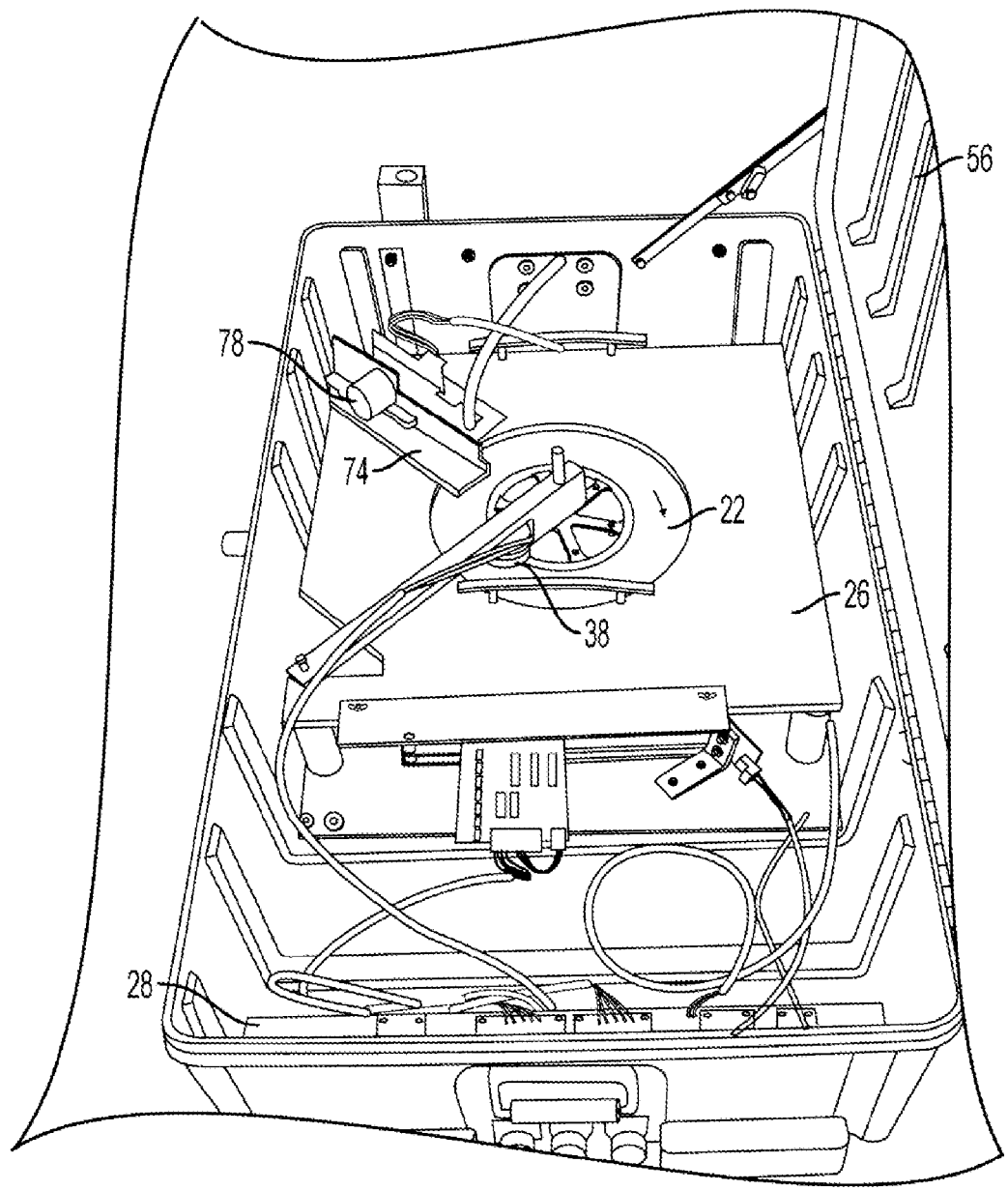
FIG. 3 illustrates a sealing plate with a low-friction surface resting on top of the carousel of FIG. 2.
Figure 4:
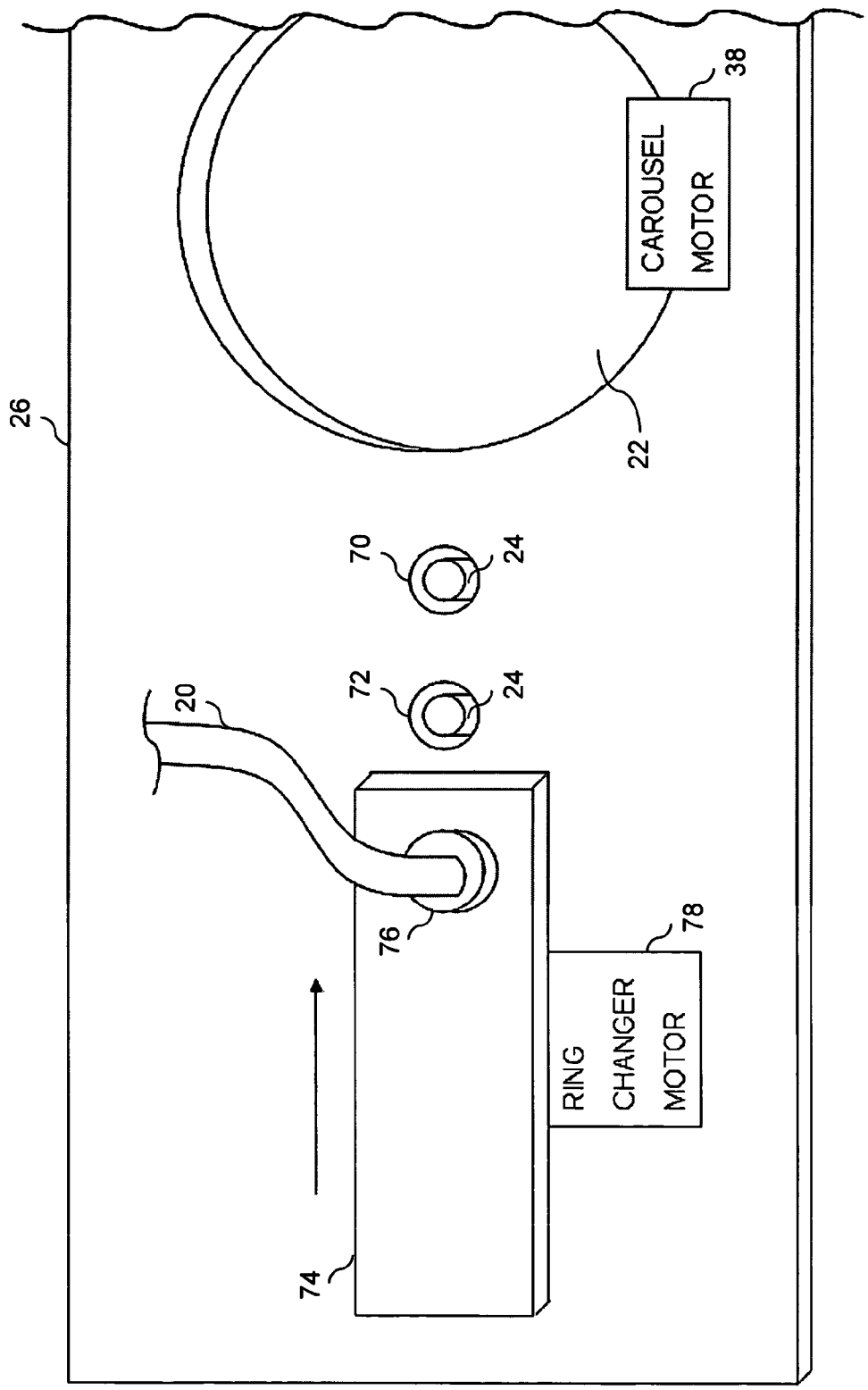
FIG. 4 illustrates a sample delivery system for the multi-sample carousel of FIG. 2.

The filling of the sample vials 24 is described in greater detail by referring to FIGS. 2 through 4. FIG. 2 shows the tops of the vials 24 in the carousel 22, according to one embodiment of the present invention. In FIG. 2, 96 20-mL vials 24 are arranged in three concentric rings, including an inner ring 50, a middle ring 52, and an outer ring 54. Each ring contains 32 vials. As shown in FIG. 3, the sealing plate 26 is placed on top of the carousel 22, with the low-friction lower surface resting on top of the sample vials 24. The sealing plate 26 includes three holes (each hole about ½-inch in diameter, for example) that correspond, respectively, to each ring of vials 24. FIG. 4 shows these holes as an inner hole 70, a middle hole 72, and an outer hole 76. The transfer line 20 is connected to one end of a vial filler 74, which initially positions the transfer line 20 over the outer hole 76. The sample vials 24 in the outer ring 54 are filled first. After each vial 24 in the outer ring 54 has been filled, the carousel 22 rotates to the next empty vial 24 in the outer ring 54, which rotates the filled vial 24 underneath the sealing plate 26 to seal the filled vial 24. After all the vials 24 in the outer ring 54 have been filled, a ring-changer motor 78 moves the vial filler 74 to position the transfer line 20 over the hole 72 for the middle ring 52, while the portion of the vial filler 74 extending away from the transfer line 20 covers and seals the hole 76 for the outer ring 54. The lower surface of the vial filler 74 is also a low-friction surface, such as a Teflon® sheet. After the vials 24 in the middle ring 52 have been filled, the ring-changer motor 78 moves the vial filler 74 to position the transfer line 20 over the hole 70 for the inner ring 50, which covers and seals the hole 72 for the middle ring 52. After the vials 24 in the inner ring 50 have been filled, the ring-changer motor 78 moves the vial filler 74 further inward to a final position, which covers and seals the hole 70 for the inner ring 50. Thus, all of the vials 24 are sealed from the time each one is filled until the vials 24 are removed from the collector 10. The number of vials and rings can be varied depending on the requirements of a specific application. Thus, more vials can be added for an extended collection period, such as 1 to 2 weeks.

An IR optical interrupter detector, for example, is used to indicate when each vial 24 is in the proper position for filling. Additional IR detectors can be used to indicate the vial number (i.e., 1 to 96 for the embodiment shown in FIG. 2). Reed switches, for example, are used for sequencing the operation of the collector 10 (e.g., moving from one ring to the next).

Figure 5:
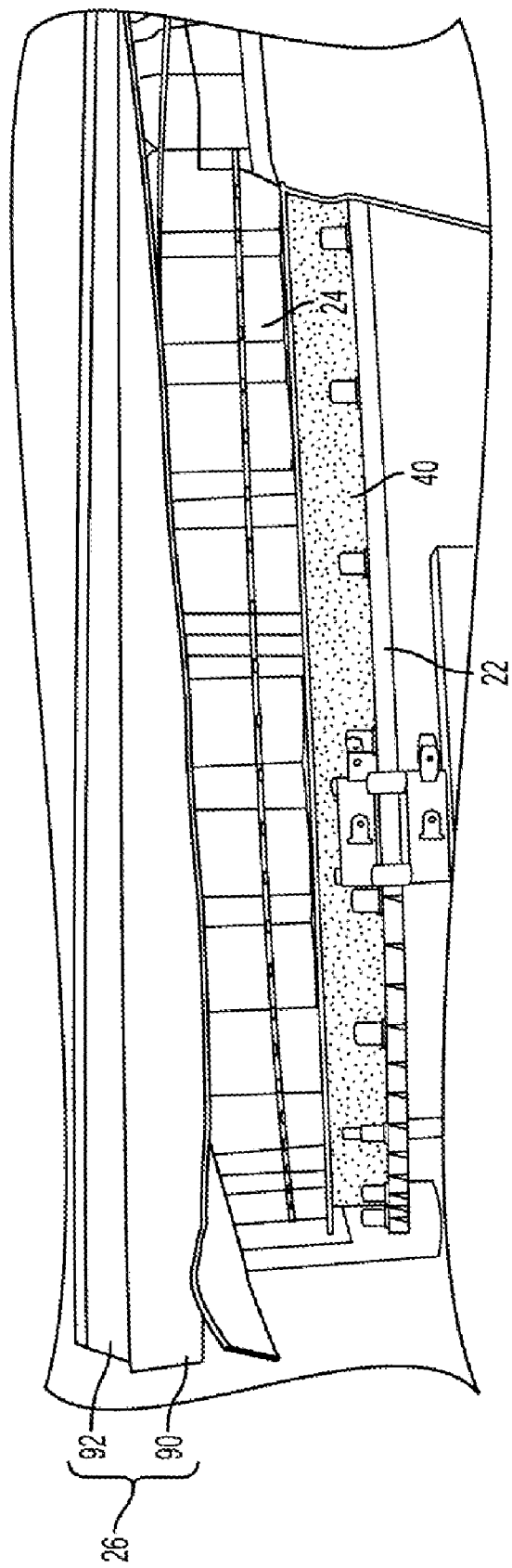
FIG. 5 is a side view of the multi-sample carousel of FIG. 2 showing the sample vials sitting on foam rubber, and components of the sealing plate of FIG. 3 used to seal the sample vials.

Isotopic fractionation of each water sample is minimized or eliminated by pressing the mouth of each sample vial 24 against the flat, low-friction surface of the sealing plate 26 to seal the mouths of the sample vials 24. Referring to FIG. 5, the sealing plate 26 may include, for example, a 20-inch×20-inch Teflon® sheet 90 bonded to a %-inch flat aluminum plate 92. In FIG. 5, the Teflon® sheet 90 has not yet been bonded to the aluminum plate 92. Each vial 24 is only exposed during the brief interval when a water sample is transferred into it. Pressure is applied to the bottom of each vial 24 by foam rubber 40 (see FIGS. 1 and 5), for example, to press each vial 24 against the Teflon® sheet. Alternatively, a spring (not shown) may be used to press each vial 24 gently, but snuggly, against the low-friction surface 26.

In addition to collecting precipitation samples, the collector 10 of the present invention can be used for collecting time-integrated water samples from wells, streams, or other dynamic sources. For these applications, a pump (not shown), such as a peristaltic pump, is used to draw water from a well or surface-water body. The flow rate is adjusted so that the first funnel 12 is only partially filled during each identical preset time interval. To maintain the integrating aspect of the collector 10, the flow rate of the pump is set so that the pump slowly trickles water into the first funnel 12 continuously over the whole time interval, without the first funnel 12 overflowing.

By using plastic vials 24, the collector 10 of the present invention may also collect samples for dissolved nitrate, which can subsequently be analyzed for concentration, nitrogen and oxygen relative isotope-amount ratios. Such measurements are useful in atmospheric and environmental investigations.

Figure 6:
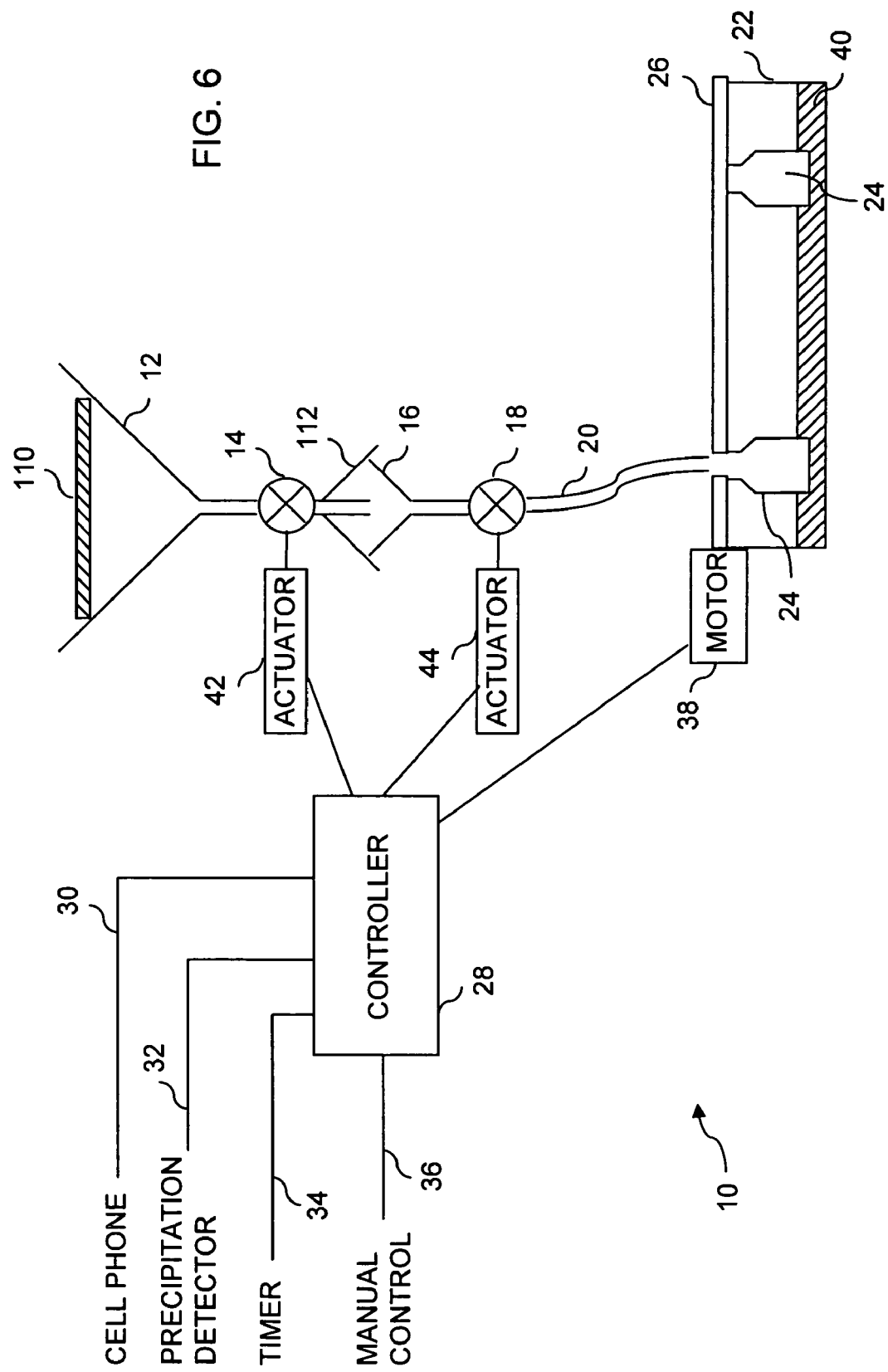
FIG. 6 illustrates a screen for a first reservoir and a shield for a second reservoir for the collector of FIG. 1.

Referring to FIG. 6, a screen 110 may be placed on top of or within the first funnel 12 to block debris from entering it. A cartridge heater and temperature sensor (not shown) can be mounted on the screen 110 to determine the time-integrated value of the relative amounts of oxygen and hydrogen isotopes in snow or hail. When the temperature is below 33° F., the temperature sensor closes, applying power to the cartridge heater, which melts any snow or hail on the screen 110. Also, a shield, such as an inverted funnel 112, may be placed over the second funnel 16 to shield it from debris or from water that might enter the second funnel 16 from a source other than the first funnel 12.

The present invention can be battery or solar powered, and the exact dates and times of collections can be recorded digitally. Also, the present invention can be set to collect precipitation samples from one storm, go into a sleep mode, and start collecting again when precipitation from the next storm is sensed. While in a sleep mode, the funnel 12 can be automatically covered with a cap (not shown) to prevent dirt, blowing sand, and debris from falling into the funnel 12.

In another embodiment of the present invention, the collector 10 can be used to monitor a tipping bucket rain gauge, which then serves as a start and stop signal for the collector 10. A tipping bucket rain gauge typically tips every 0.01 inch of rain. When it tips, it activates a switch (such as a reed switch) to electronically record both rain rate and accumulation. This embodiment of the present invention provides time-integrated samples of precipitation for analysis, as well as an accurate time record of precipitation, and the controller 10 can be set to collect samples only when the tipping bucket rain gauge rate is greater than a preset amount. Thus, in this embodiment, the sample vials 24 would not be wasted during a period (e.g., 24 hours) when a very light mist was falling.

Advantages of the present invention include the ability to collect a large number of samples (e.g., 96 or more samples) over an extended period of time (e.g., 48 hours or longer). Small samples (e.g., 0.5 mL) can be collected without isotopic fractionation resulting from evaporation of the sample. Also, each sample collected is representative of the entire time interval (i.e., time-integrated) during which water is collected that becomes the source from which the sample is drawn.

Thus, it will be appreciated by those skilled in the art that modifications and variations of the present invention are possible without departing from the principles and spirit of the invention, the scope of which is defined in the appended claims and their equivalents.

What is claimed is:

1. A water collector for collecting multiple sequential, time-integrated water samples over multiple preset time intervals, comprising:
    a first reservoir receiving and holding water therein during a preset time interval, the preset time interval having a start time and a start time;
    a first valve connected to the first reservoir, the first valve being closed during the preset time interval so that the first reservoir can hold the water;
    a second reservoir, connected to the first valve, receiving a predetermined amount of a water sample from the water in the first reservoir at the end of the preset time interval, the first valve opening when the stop time of the preset time interval is reached to transfer the water sample from the first reservoir to the second reservoir, any excess water being discharged from the second reservoir;
    a second valve connected to the second reservoir;
    a transfer line having a first end and a second end, the first end being connected to the second valve;
    a carousel containing a plurality of vials, the plurality of vials comprising a first vial and a plurality of second vials;
    a single sealing plate resting simultaneously on top of the plurality of vials on the carousel, the sealing plate having a first opening under which the first vial is positioned, the second end of the transfer line being positioned above the first opening and the second valve being opened after the second reservoir receives the water sample to transfer the water sample through the transfer line to the first vial, the carousel rotating immediately after the first vial receives the water sample from the second reservoir to move the first vial away from the first opening and underneath the sealing plate, a top of the first vial contacting a bottom surface of the sealing plate to seal the first vial, while moving one of the second vials underneath the first opening to receive a next water sample over a next preset time interval,
    wherein the carousel rotates after each of the second vials has been filled at the end of each successive preset time interval until all of the vials have received a separate water sample and have been sealed by the carousel rotating each vial under the sealing plate after being filled to prevent evaporation of the water sample in each vial.

2. The water collector of claim 1, further comprising a controller to control opening and closing of the first valve and the second valve and rotation of the carousel, the controller receiving a start signal from one of a timer, a precipitation sensor, a cell phone, and a manually-controlled button on the controller.

3. The water collector of claim 1, further comprising foam rubber on which each of the plurality of vials rests, wherein a mouth of each of the vials is pressed against the sealing plate by pressure applied to a bottom of each of the vials by the foam rubber.

4. The water collector of claim 1, wherein:
    the carousel further comprises a vial filler;
    the sealing plate further comprises one or more additional openings;
    the plurality of vials are arranged in one or more concentric rings on the carousel;
    the vial filler has an opening to which the transfer line is attached, and the opening of the vial filler is initially positioned over the first opening on the sealing plate;
    each one of the first opening and the one or more additional openings corresponds to one of the rings, the first opening corresponding to a first one of the rings;
    after one of the vials in the first ring has been filled through the first opening, the carousel rotates the filled vial underneath the sealing plate and rotates a next empty vial in the first ring underneath the first opening; and
    after all vials in the first ring have been filled, the vial filler moves over the first opening on the sealing plate, sealing the first opening, and positions the transfer line over a next one of the openings for a next one of the rings, wherein all the vials in each of the rings is successively filled and sealed, with the vial filler successively moving to each one of the rings to fill and seal all the vials in each ring.

5. The collector of claim 1, wherein the sealing plate comprises an aluminum plate and a sheet having a low-friction surface bonded to a bottom of the aluminum plate, the low-friction surface sheet contacting the plurality of vials.

6. The collector of claim 1, wherein the first reservoir captures water over a preset time interval of about 30 minutes.

7. The collector of claim 1, wherein at least 96 vials are placed in the carousel.

8. The collector of claim 1, where a volume of the first reservoir is about 1,000 mL, a volume of the second reservoir is about 15 mL, and a volume of each of the plurality of vials is about 20 mL.

9. The collector of claim 1, wherein a volume of the second reservoir is about 75% of a volume of each of the plurality of vials.

10. The collector of claim 1, wherein a volume of each of the plurality of vials is greater than a volume of the second reservoir.

11. The collector of claim 1, wherein a volume of each of the water samples is about 0.5 mL.

12. The collector of claim 1, wherein the collector is used to collect one of precipitation, surface water, and ground water.

13. The collector of claim 1, further comprising:
a controller to control opening and closing of the first valve and the second valve and rotation of the carousel; and
a tipping bucket rain gauge sending a start signal and a stop signal to the controller to control starting and stopping of the collector, the collector collecting water samples when a rate of the tipping bucket rain gauge is greater than a preset amount.

* * * * *